(12) United States Patent
Lukas (10) Patent No.: US 8,715,724 B2
(45) Date of Patent: May 6, 2014

(54) TABLETTING PROCESS

(75) Inventor: Stefan Lukas, Manningham (AU)

(73) Assignee: Mayne Pharma International Pty Ltd, Melbourne, Victoria (AU)

( * ) Notice: Subject to any disclaimer, the term of this patent is extended or adjusted under 35 U.S.C. 154(b) by 828 days.

(21) Appl. No.: 11/666,354

(22) PCT Filed: Oct. 28, 2005

(86) PCT No.: PCT/AU2005/001663
§ 371 (c)(1),
(2), (4) Date: Jun. 26, 2007

(87) PCT Pub. No.: WO2006/045152
PCT Pub. Date: May 4, 2006

(65) Prior Publication Data
US 2009/0136568 A1 May 28, 2009

(30) Foreign Application Priority Data
Oct. 29, 2004 (AU) .................................. 2004906219

(51) Int. Cl.
| | | |
|---|---|---|
| A61K 9/20 | (2006.01) |
| A61J 3/10 | (2006.01) |
| A61K 31/65 | (2006.01) |
| A61K 47/02 | (2006.01) |
| A61K 47/10 | (2006.01) |
| A61K 47/12 | (2006.01) |
| A61K 47/36 | (2006.01) |
| A61K 47/38 | (2006.01) |

(52) U.S. Cl.
USPC .......... 424/464; 424/490; 427/185; 514/152; 514/770; 514/781; 514/784; 514/785

(58) Field of Classification Search
None
See application file for complete search history.

(56) References Cited

U.S. PATENT DOCUMENTS

| | | | |
|---|---|---|---|
| 4,347,235 A | | 8/1982 | Daunora |
| 4,684,516 A | * | 8/1987 | Bhutani .......................... 424/469 |
| 4,966,770 A | | 10/1990 | Giannini et al. |
| 5,009,897 A | | 4/1991 | Brinker et al. |
| 5,169,642 A | | 12/1992 | Brinker et al. |
| 5,268,182 A | | 12/1993 | Brinker et al. |
| 5,288,501 A | | 2/1994 | Nurnberg et al. |
| 5,468,286 A | | 11/1995 | Wai-Chiu et al. |
| 6,054,145 A | | 4/2000 | Vromans et al. |
| 6,346,269 B1 | * | 2/2002 | Hsiao et al. .................... 424/472 |
| 6,669,879 B1 | | 12/2003 | Spengler et al. |

(Continued)

OTHER PUBLICATIONS

Hill, Philip M., "Effect of Compression Force and Cron Starch on Tablet Disintegration Time" Journal of Pharmaceutical Sciences, Nov. 1976, 65(11): pp. 1694-1697.*

(Continued)

Primary Examiner — Brian-Yong Kwon
Assistant Examiner — Christopher R Lea
(74) Attorney, Agent, or Firm — Cooley LLP (57) ABSTRACT

A process for producing a compressed solid dosage form containing an active ingredient. The process includes a step of preparing core elements containing the active ingredient. Optionally the core elements are coated with a pharmaceutically acceptable coating layer to form coated pellets. The core elements or pellets are treated with an anti-static agent and compressed with suitable excipients to form the compressed solid dosage form. Preferred anti static agents are starch, microcrystalline cellulose, kaolin, bentonite, silicates, silicon dioxide, cellulose, stearic acid, sodium stearyl fumarate and glyceryl behenate.

23 Claims, 2 Drawing Sheets

(56) References Cited

U.S. PATENT DOCUMENTS

| | | |
|---|---|---|
| 6,723,348 B2 | 4/2004 | Faham et al. |
| 2003/0099700 A1 | 5/2003 | Faham et al. |
| 2005/0053654 A1 | 3/2005 | Faham et al. |

OTHER PUBLICATIONS

Pharmaceutical Dosage Forms, Tablets, 2nd Edition, 1989, vol. 1, Edited by Herbert A Lieberman et al., Marcel Dekker, Inc., New York, USA. (see in particular Chapter 1 Preformulation Testing, Wadke, D.A. et al., p. 55 last 4 lines to p. 56 line 2, Chapter 2 Tablet Formulation and Design, Peck, G.E. et al., pp. 110-116 and Chapter 3, Compressed Tablets by Wet Granluation, Bandelin, F.J., pp. 169-179.).

Pharmaceutical Dosage Forms, Tablets, 2nd Edition, 1990, vol. 2, Edited by Herbert A. Lieberman et al., Marcel Dekker, Inc., New York, USA. (see in particular Chapter 5 Granulation Technology and Tablet Characterization, Gordon, R.E. et al., pp. 295-298 and pp. 306-308.).

Jones, T.M., The effect of glidant addition on the flowability of bulk paticulate solids, J. Soc. Cosmet. Chem., (1970), vol. 21, pp. 483-500. (see in particular Table III on pp. 488-489, and p. 496.).

Bravo, S.A., et al., In-vitro studies of diclofenac sodium controlled-release from biopolymeric hydrophilic matrices, J. Pharm. Pharmaceut. Sci., (www.ualberta.ca/~csps) (2002), vol. 5, No. 3, pp. 213-219.) (see in particular "Materials and methods," Preparation and characterization of matrix tablets, and "Results and The matrix tablets.").

Cabot, Applications of Cab-O-Sil® M-5P Fumed Silica in the Formulation and Design of Solid Dosage Forms. (see in particular the Summary), (2004).

Cabot, Properties of Cab-O-Sil® M-5P Fumed Silica. (see in particular the passage entitled "Flow Properties."), (2004).

Cabot, Influence of Cab-O-Sil® M-5P on the angle of Repose and flow Rates of Pharmaceutical Powders. (see in particular the second paragraph in passage entitled "Background.") (2004).

* cited by examiner

TABLETTING PROCESS

FIELD OF THE INVENTION

The present invention relates to processes for the production of solid dosage forms, such as tablets, containing an active ingredient.

BACKGROUND OF THE INVENTION

Solid dosage forms such as capsules and tablets are widely used for delivering active ingredients such as drugs to a person or animal in need of treatment. The main advantage of solid dosage forms is that they are readily administered orally which results in a high level of patient compliance. Similarly, solid dosage forms are used to deliver active ingredients such as agrochemicals into biological systems such as plants, soil strata and natural water bodies.

Solid dosage forms can be produced by forming core elements containing an active ingredient. The core elements may be coated with agents such as pharmaceutically acceptable polymers to form pellets wherein the in situ release profile of the active ingredient is modified by the coating. The core elements or pellets may then be filled directly into hard gelatin capsules, or, alternatively combined with suitable binders and other tablet excipients and compressed to form tablets.

The present invention is primarily concerned with compressed solid dosage forms such as tablets. A build up of static charge is a significant problem during tablet formation using the processes just described. The build up of static charge during core element or pellet formation can interfere with handling and processing of the core elements or pellets. For example, it is generally necessary to remove both over and under size pellets by sieving, and a build up of static charge can interfere with the flowability of the core elements or pellets being sieved. It is also important that the flow of core elements or pellets between a hopper containing the core elements or pellets and a tablet press is uniform and predictable and a build up of static charge can interfere with that flow.

To reduce accumulated static charge or prevent or reduce accumulation of static charge during core element and pellet formation talc in powder form has conventionally been admixed with pellets in small concentrations (≤0.5% w/w). Whilst this talc admixing procedure has been found to be very effective in the case of sieving and subsequent capsule filling, it has been found that treating the pellets with talc in this way is unsuitable when the pellets are to be incorporated into tablets because the resulting tablets are too friable.

The present invention provides processes for producing core elements and pellets that can be used to form tablets but which reduce problems associated with a build up of static charge during core element and pellet formation and subsequent processing. The processes of the invention do not adversely affect tablet formation.

Before turning to discuss the present invention, it should be appreciated that the above discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed in any particular country before the priority date of each claim of this application.

SUMMARY OF THE INVENTION

The present inventor has discovered that a range of materials are effective in reducing accumulated static charge or preventing or reducing accumulation of static charge during core element and pellet formation and subsequent processing. The materials that have been identified also do not adversely affect compressibility of a tablet blend containing core elements or pellets that have been treated with the material. The compressibility of a tablet blend affects the friability of a resultant tablet. There is a requirement for a tablet to be hard enough to not disintegrate during handling and shipping, but still be able to disintegrate or dissolve when placed in the appropriate environment, such as in the intestinal tract. The materials identified herein are able to be used as anti-static agents for core elements or pellets for tablets and the resulting tablets are not too friable for normal handling and use.

The present invention provides a process for producing a compressed solid dosage form containing an active ingredient. The process includes:
    preparing core elements containing the active ingredient,
        optionally coating the core elements with a pharmaceutically acceptable coating layer to form coated pellets,
        treating the core elements or pellets with an anti-static agent, and
        compressing the treated core elements or pellets with suitable excipients to form the compressed solid dosage form,
wherein the hardness of the compressed solid dosage form is greater for a given compression force than an equivalent solid dosage form in which the core elements or pellets have been treated with talc.

The step of treating the core elements or pellets with an anti-static agent preferably reduces accumulated static charge or prevents or reduces accumulation of static charge.

Preferably, the step of preparing the core elements or the step of applying a coating is followed by a step of drying the core elements or pellets to remove a desired amount of residual solvent used in the core element preparation or the coating steps. In this preferred form of the invention, the step of treating the core elements or pellets with an anti-static agent may be carried out during the drying step or after the drying step.

In a preferred form of the invention, the anti-static agent is admixed with the core elements or pellets in particulate form. Most preferably, the anti-static agent is in powdered form. The anti-static agent may be added manually or it may be added in an air stream. In the case of a powdered ant-static agent, the step of treating the core elements or pellets with the anti-static agent may also be referred to as dusting the core elements or pellets.

The anti-static agent used in the process of the present invention may be any inorganic or organic solid that reduces static but still allows cohesion between core elements or pellets and excipients in the solid dosage form in order for it to retain strength and structure. Materials having anti-static properties may be in a powdered form (i.e. a particle size less than about 250 microns) and be pharmaceutically acceptable. Examples of suitable materials may include, but not be limited to, polysaccharides, minerals, clays, organic acids, silicates, silicon dioxide, stearates, fumarates, and glyceryl esters. Preferably, the anti-static agent is selected from the list including starch, microcrystalline cellulose, kaolin, bentonite, magnesium trisilicate, aluminium trisilicate, silicon dioxide, cellulose, stearic acid, sodium stearyl fumarate, and glyceryl behenate.

The present invention also provides a process for producing a compressed solid dosage form containing an active ingredient, the process including:
    preparing core elements containing the active ingredient, optionally coating the core elements with a pharmaceutically acceptable coating layer to form coated pellets, treating the core elements or pellets with a powdered anti-static agent, and compressing the treated core elements or pellets with suitable excipients to form the compressed solid dosage form, wherein the anti-static agent is not talc.

Preferably, the anti-static agent is selected from the list including starch, microcrystalline cellulose, kaolin, bentonite, silicates, silicon dioxide, cellulose, stearic acid, sodium stearyl fumarate and glyceryl behenate.

The present invention further provides a method of reducing accumulated static charge or preventing or reducing an accumulation of static charge during formation of a solid compressed dosage form, the method including the step of treating core elements or coated pellets with a powdered anti-static agent selected from the list including starch, microcrystalline cellulose, kaolin, bentonite, silicates, silicon dioxide, cellulose, stearic acid, sodium stearyl fumarate, and glyceryl behenate, to reduce accumulated static charge or reduce or prevent accumulation of static charge during or after drying of the core elements or pellets.

The present invention still further provides a process for producing a tablet suitable for oral administration, the process including the steps of:

granulating a powdered pharmaceutically active ingredient and optionally powdered excipients to form a wet granulate, extruding and marumerising the wet granulate to form core elements, removing a desired amount of solvent from the core elements, applying a rate controlling membrane to the core elements in a fluid bed to form pellets, drying the pellets, dusting the pellets with an anti-static agent at the completion of coating to reduce the static charge accumulated during the coating and drying process, sieving the pellets, blending the dusted and sieved pellets with suitable tablet excipients, transferring the blend to a tablet press, and compressing the blended pellets and tablet excipients to form the tablet, wherein the anti-static agent is selected from the list including starch, microcrystalline cellulose, kaolin, bentonite, silicates, silicon dioxide, cellulose, stearic acid, sodium stearyl fumarate, and glyceryl behenate.

The present invention still further provides a compressed solid dosage form, such as a tablet, that is formed using a process of the present invention.

DESCRIPTION OF THE INVENTION

Various terms that will be used throughout this specification have meanings that will be well understood by a skilled addressee. However, for ease of reference, some of these terms will now be defined.

The term "active ingredient" will be widely understood and denotes a compound having a beneficial effect when introduced into a system such as a biological system. For example, the active ingredient may be a biologically active compound for introduction into a human, animal, plant, water body or soil strata. Examples of biologically active compounds for this purpose include pharmaceutically active ingredients and agrochemicals. Exemplary agrochemicals include fertilisers, nutrients, pesticides, fungicides and algaecides. Pharmaceutically active ingredients include any compound that provides prophylactic and/or therapeutic properties when administered to, for example, humans. Examples include, but are not limited to, pharmaceutical actives, therapeutic actives, veterinarial actives, nutraceuticals, and growth regulators. Reference in this specification to a specific active ingredient is also to be understood to include the active ingredient in the form of acid addition salts, solvates, hydrates and the like.

As used herein, the term "core element" will be understood to mean un-coated particles containing a mixture of one or more active ingredients and excipients. These may be produced by, for example, granulation or spray drying of mixtures of active ingredients and excipients, or by applying a layer of the active ingredient over inert cores. The term "pellets" as used herein will be understood to mean coated core elements. Typically, the coating will be a modified release coating. It will be appreciated that the process of the present invention may be applied to core elements and/or pellets.

As used herein, the term "coating" will be understood to include either complete or partial coating of the surface of a core element to form a pellet.

As used herein, the term "treating" in reference to the addition of anti-static agents to core elements or pellets will be understood to mean the step of adding an anti-static agent to a collection of core elements or pellets in any suitable manner. When the anti-static agent is in particulate or powdered form, the step of treating may be referred to as dusting the core elements or pellets.

As used herein, the term "compressed solid dosage form" will be understood to mean any dosage form that is prepared by compressing solid ingredients together into a single unit. The compressed solid dosage form may be shaped. Compressed solid dosage forms include tablets and caplets.

As described previously, the present invention provides a process for producing compressed solid dosage forms containing an active ingredient. To produce compressed solid dosage forms, such as tablets, a mixture containing an active ingredient (eg. a drug) and excipients may be granulated to form core elements. The granulation process may be a "wet granulation" process which means that water or other solvent is used in the granulation step. An alternative process for producing a core element is to apply a layer of active ingredient over inert cores. The layer of active ingredient may be applied by spraying a solution of the active ingredient onto the inert cores. A drying step may be used to remove some or all of the solvent from the core element.

The core elements formed by either of these processes may be incorporated directly into a solid dosage form or they may first be coated with a pharmaceutically acceptable coating layer to form pellets. This coating step may be performed to confer controlled release or other properties onto the pellets. Thus, the core elements to be coated may be suspended in an air stream while a coating material (usually dissolved or suspended in a suitable liquid vehicle or solvent) is atomised onto the core elements to form the coated pellets. A drying step may be used to remove some or all of the solvent from the pellets.

The core elements or pellets thus formed are then incorporated into the solid dosage form. In the case of a tablet, they may be blended with tablet excipients and then pressed into the form of a tablet. The core elements or pellets are preferably treated with an anti-static agent at or after a drying step to reduce accumulated static charge or to prevent or reduce accumulation of static charge.

Formation of Core Elements

The first step in the process of the present invention is the preparation of core elements containing the active ingredient. In a preferred embodiment, this involves a process of granulation, extrusion, and marumerisation using the active ingredient and suitable excipients to form a plurality of core elements containing the active ingredient. An alternative is to apply a layer of the active ingredient onto inert cores to form core elements containing the active ingredient.

To form the core elements consecutive steps of wet granulation, extrusion and marumerisation are described herein (see Example 1). However, the person skilled in the art will appreciate that any of a number of techniques may be used, such as spheronisation onto seed cores, or rotogranulation.

The active ingredient is preferably a pharmaceutically active compound or chemical compound suitable for medicinal or diagnostic use. For example, the active ingredient may be selected from the list consisting of doxycycline, tetracycline, oxytetracycline, minocycline, chlortetracycline, demeclocycline, and pharmaceutically acceptable salts thereof. However, the dosage forms that are produced by the methods of the present invention are not limited to the aforementioned active ingredients. Indeed, the present invention is not dependent on the nature of the active ingredient and therefore the processes described herein may be applied to any compressed solid dosage form containing core elements or pellets. For example, it is envisaged that a wide variety of classes of active ingredients such as anti-hypertensives, immunosuppressants, anti-inflammatories, diuretics, antiepileptics, cholesterol lowering drugs, hormonals, hypoglycemics, antiviral drugs, nasal decongestants, antimicrobials, anti-arthrytics, analgesics, anti-cancer drugs, anti-parasitics, proteins, peptides, CNS stimulants, CNS depressants, 5-HT inhibitors, anti-schizophrenics, anti-Alzheimer drugs, anti-psoriatics, steroidals, oligonucleotides, anti-ulcer drugs, proton pump inhibitors, anti-asthmatics, thrombolytics and vitamins may be suitable.

The active ingredient may be present in the core element in any suitable amount, and for instance may be provided in an amount from 5 to 95% by weight, preferably from 20 to 80% by weight, based on the total weight of the core element.

The active ingredient may be embodied within and through the core element, combined with or without the normal excipients, additives and fillers. Preferably, the core elements each have a diameter in the range of 50 microns to 1700 microns. In one particularly preferred form of the invention the core elements each have a diameter in the range of 500 microns to 1000 microns.

The core elements may contain any suitable or required additives, such as excipients, fillers or other ingredients. For example, modified release core elements may be formed by granulating the active ingredient with insoluble materials such as waxes or insoluble polymers.

Formation of Coated Pellets

The core elements may be coated with a coating to form pellets. A coating may be applied for a number of reasons, such as, masking a bitter taste, or altering the rate of release (dissolution) of the active ingredient. Preferably, the core elements are coated to provide a modified release profile. The modified release coating may be any suitable coating material, or combination of coating materials, that will provide a desired modified release profile. For example, coatings such as enteric coatings, semi-enteric coatings, delayed release coatings or pulsed release coatings may be desired. A mixture of enteric polymers may be used to produce a modified release coating. It is possible to use a mixture of enteric polymer with a water permeable, water swellable or water-soluble material such as polyvinylpyrrolidone, hydroxypropyl cellulose, hydroxypropyl methylcellulose, polyethylene glycol having a molecular weight of from 1700 to 20,000, or a mixture thereof. The coating could also be a water-insoluble material, such as ethylcellulose, and/or enteric polymers such as cellulose acetate phthlate, hydroxypropyl methylcellulose phthalate (HPMCP), polyvinyl acetate phthalate, methacrylic acid copolymer, hydroxypropyl methylcellulose acetate succinate, shellac, cellulose acetate trimellitate, or a mixture thereof. In particular, materials such as hydroxypropylmethyl cellulose, hydroxypropylmethyl cellulose phthalate of varying grades and also as an aqueous dispersion, Eudragit® L100-55, Eudragit® L30D, and hydroxypropylmethyl cellulose acetate succinate may be used to form the modified release coating. The coating may also contain plasticisers such as triethyl citrate, diethyl phthalate or dibutyl sebacate.

The core elements may be coated by spray drying; spray congealing; coacervation; fluid bed coating (also known as spray coating where the coating is sprayed onto the pellet), including Wurster coating, and rotacoating. In most cases, the coating material will be dissolved or dispersed in a solvent or other carrier.

The weight of coating (as a percentage of the total coated pellet) will vary depending on the delay desired and the coating used, but generally will be between 5% w/w and 20% w/w, wherein the weight of the coating is the weight of the polymer and plasticiser in the coating layer and does not include additives which do not significantly affect the release rate of the pellet.

The coating may be formed from a plurality of layers. The combination of various layers such as a coating layer not containing the active ingredient, a base coating layer, and an enteric coating layer which constitute the coating layer may be suitable.

Drying of Core Elements and/or Pellets

Following formation of the core elements (and before coating) a drying step is ordinarily used to remove a desired amount of the solvent present. Typically, the solvent will be water although other solvents may also be used. The drying step may be carried out using a fluid bed dryer or a tray dryer.

If the core elements are coated to form pellets, it will generally also be necessary to include a drying step after the coating step. This is to remove a desired amount of the solvent that is used in the coating step. Again, the drying step may be carried out using a fluid bed dryer.

It is during the aforementioned drying steps that a significant build up of static charge can occur.

Treatment of Core Elements and/or Pellets with an Anti-static Agent

Either during or directly after either of the aforementioned drying steps, the core elements or pellets are treated with an anti-static agent, such as starch or magnesium trisilicate, to reduce accumulated static charge or to prevent or reduce accumulation of static charge during processing and handling of the core elements or pellets.

The anti-static agent is an organic or inorganic solid that reduces static without substantially affecting compressibility of a blend containing core elements or pellets to which it has been added. Preferably, the anti-static agent is selected from the list including starch, microcrystalline cellulose, kaolin, bentonite, silicates (such as magnesium trisilicate and aluminium trisilicate), silicon dioxide, cellulose, stearic acid, sodium stearyl fumarate, and glyceryl behenate.

It has been found that by using the anti-static agents disclosed herein it is possible to treat the core elements or pellets to prevent or reduce accumulation of static charge or to discharge some of the accumulated static charge whilst still being able to form a compressed solid dosage form, in particular a tablet, that has the required degree of structural integrity such that the dosage form can be handled and transported in the usual manner without the tablet breaking up. This is believed to be a result of the surprising finding that certain organic and inorganic pharmaceutical excipients have either no effect or a positive effect on the compressibility of a blend of core elements or pellets and tabletting excipients so as to allow for the formation of more robust tablets. In contrast, talc has been found to have a significantly negative effect on compressibility. It is thought that whilst talc is very effective at controlling static it acts as a glidant between particles and decreases cohesion between excipients and core elements or pellets. This cohesion is required in order for the tablet to retain strength and structure.

Tablet Formation

After formation and treatment with an anti-static agent, the core elements or pellets are passed through sieves to obtain core elements or pellets of defined size range. A relatively narrow size range is desirable when a uniform rate of drug release is desirable. It depends on the individual situation, but generally, coated pellets in the range 50 microns to 2000 microns, preferably 500 to 1180 microns are desired.

The sieved core elements or pellets are then compressed optionally with suitable excipients to form the compressed solid dosage form. The hardness of the compressed solid dosage form is greater for a given compression force than an equivalent solid dosage form in which the pellets have been treated with talc. The inventor has found that the compressibility of a blend of core elements or pellets and excipients can be significantly affected depending on the choice of antistatic agent. Compressibility is defined herein as the relationship between the force applied during compression in a tablet press and the hardness (or breaking strength) of the resultant tablet. High compressibility is when high tablet hardness can be attained with comparatively low to moderate compression forces. It will be appreciated that the higher the compression force used in tablet formation, the more likely it is that the release of the active agent from the pellet will be adversely affected and/or any coating on the pellet may be fractured. For this reason, lower compression forces (ie. high compressibility) are favoured. Preferably, the compression force at which the solid dosage form is formed is less than 40 kiloNewtons.

To determine whether the hardness of the compressed solid dosage form is greater for a given compression force than an equivalent solid dosage form in which the core elements or pellets have been treated with talc it is possible to compress the subject core elements or pellets with suitable excipients at a given compression force and then measure the hardness of the tablet using the methods described in Example 2 herein.

The core elements or pellets may be dry blended with suitable tablet excipients before being transferred to a tablet press and pressed into tablets using standard tabletting procedures. The dry ingredients may be tabletted by using a single-punch tablet machine or a rotary type tablet machine.

Suitable tabletting excipients will be known to a person skilled in the art. The person skilled in the art will also appreciate that the proper formulation of a tablet involves balancing the need for content uniformity (i.e. making sure the same number of core elements or pellets is present in each tablet and therefore the same amount of active ingredient is present in each tablet) and the friability of any tablet that is formed as well as protection of coated pellets from fracture of the coating during the tabletting step. In this respect, if the weight ratio of core elements or pellets to excipients is too low, there will be problems with content uniformity, while if the weight ratio of core elements or pellets is too high there will not be enough tabletting excipients to cushion the core elements or pellets during compression into a tablet and the structural integrity of the core elements or pellets could be compromised. Also, if the amount of excipients is low the core elements or pellets are more likely to be damaged during compression and the tablets will also be weak and friable because they will not have sufficient binder to hold them together. Therefore the percentage of core elements or pellets in each tablet is ideally in the range of 20 to 50% (more preferably 25 to 35%, but most preferably about 30%) by weight of the total dosage weight.

It will also be appreciated that the tablets may include a range of traditional additives such as disintegrants, diluents, fillers, lubricants, glidants, colourants and flavours in addition to the anti-static agent used in the treating step.

For example, suitable disintegrants may be those that have a large coefficient of expansion, and examples may include crosslinked polymers such as crospovidone (crosslinked polyvinylpyrrolidone) and croscarmellose (crosslinked sodium carboxymethylcellulose).

Also, it will be appreciated that it may be advantageous to add to a dosage form an inert substance such as a diluent or filler. A variety of materials may be used as diluents or fillers, and examples may be lactose, starch, sucrose, dextrose, mannitol, sorbitol, microcrystalline cellulose, and others known in the art, and mixtures thereof.

Lubricants and glidants may be employed in the manufacture of certain dosage forms, and will usually be employed when producing tablets. Examples of lubricants and glidants are hydrogenated vegetable oils, magnesium stearate, stearic acid, sodium lauryl sulfate, magnesium lauryl sulfate, colloidal silica, talc, mixtures thereof, and others known in the art.

Additives such as colouring agents and pigments may also be added to dosage forms in accordance with the present invention, and suitable colouring agents and pigments may include titanium dioxide and dyes suitable for food.

The strength of the tablet of the present invention (measurement with a tablet hardness tester) is usually about 1 to 20 kiloponds (kp), preferably about 5 to 15 kp, more preferably 7 to 15 kp, although it will be appreciated that these hardness values are dependent to some extent on the physical dimensions of the tablet.

Surprisingly, the inventor has found that there is a substantially linear relationship between the compression force and the hardness over an extended range of compression force for a tablet formed from pellets that have been treated with anti-static agents such as starch, microcrystalline cellulose, silicates such as magnesium trisilicate and kaolin relative to a tablet containing cores or pellets that have been treated with talc. Thus, at least in the case of aforementioned anti-static agents, an increase in the compression force used in tablet formation results in a concomitant increase in the hardness of the resulting tablet over a larger range of compression force values than talc. This results in the advantage that the peak hardness for these compounds is greater than for talc, and that a broader range of hardness values can be obtained by using a greater range of compression forces. In the case of talc the peak hardness that can be attained is lower.

Tablets that are formed using the processes of the present invention may be administered without water or together with water. For example, they may be administered by dissolution or disintegration with water, or without water and with saliva in the oral cavity, or they may be swallowed as is. The tablets can be administered at a suitable dosing interval.

It will be appreciated from the foregoing discussion that a preferred example of the process of the present invention comprises:
  granulating a powdered pharmaceutically active ingredient and optionally powdered excipients to form a wet granulate,
  extruding and marumerising the wet granulate to form core elements,
  removing a desired amount of solvent from the core elements,
  applying a rate controlling membrane to the core elements in a fluid bed to form pellets,
  drying the pellets,
  dusting the pellets with an anti-static agent at the completion of coating to reduce the static charge accumulated during the coating and drying process,
  sieving the pellets,
  blending the dusted and sieved pellets with suitable tablet excipients,
  transferring the blend to a tablet press, and
  compressing the blended pellets and tablet excipients to form the tablet,
wherein the anti-static agent is selected from the list including starch, microcrystalline cellulose, kaolin, bentonite, silicates, silicon dioxide, cellulose, stearic acid, sodium stearyl fumarate, and glyceryl behenate.

DESCRIPTION OF EMBODIMENTS OF THE INVENTION

Reference will now be made to examples that embody the above general principles of the present invention. However, it is to be understood that the following description is not to limit the generality of the above description.

Example 1

Tablet Formulation and Process

A tablet containing the ingredients listed in Table 1 was formed.

TABLE 1

| Item # | Ingredient | % w/w | mg/tablet (75 mg doxycycline) |
|---|---|---|---|
| 1 | Doxycycline hyclate | 16.17 | 86.7 |
| 2 | Lactose monohydrate | 2.04 | 10.9 |
| 3 | Microcrystalline cellulose | 2.04 | 10.9 |
| 4 | Sodium lauryl sulphate | 0.11 | 0.6 |
| 5 | Sodium chloride | 2.13 | 11.4 |
| 6 | Hydroxypropyl methyl cellulose | 1.45 | 7.8 |
| 7 | Hydroxypropyl methyl cellulose phthalate | 3.00 | 1.7 |
| 8 | Talc | 0.32 | 16.1 |
| 9 | Triethyl citrate | 0.70 | 3.8 |
| 10 | Lactose anhydrous | 58.74 | 315.0 |
| 11 | Starch (corn starch Unipure F) | 10.00 | 53.6 |
| 12 | Crospovidone | 3.00 | 16.1 |
| 13 | Magnesium stearate | 0.30 | 1.6 |

The process for producing the tablet was as follows.

Items 1 to 4 in Table 1 above were dry blended for a short time before adding the required volume of salt solution. Blending was continued until the granulating solvent (salt solution) was evenly dispersed throughout the dry blend to form the 'wet granulate'.

The wet granulate was fed through an extruder to produce long strands of extrudate that were then broken up and rounded on the grooved plate of a 'marumeriser'. The equipment used in the above processes is readily available from a number of manufacturers in particular Fuji Paudal (Japan) and Collette (Belgium).

The wet core elements from above were then dried using a fluid bed dryer (Glatt Air Techniques, USA).

The dried core elements were then coated in a similar fluid bed equipped with a 'Wurster' tube to facilitate high speed coating. The coating was applied in two portions. The first comprised items 6 and 8 dissolved/dispersed in a mixed ethanol/water solution. The second coating comprised items 6, 7, and 9 dissolved in a similar solvent. At the end of coating (when the desired rate of drug release is reached, as tested in vitro) the pellets were dried in the fluid bed for 2 hours. At the end of drying 0.5% w/w starch was added in the fluid bed to reduce the significant static charge (built up during the drying step) prior to emptying the fluid bed and sifting the pellets.

All of the tablet excipients (items 10 to 13 above) were initially passed through an 850 micron screen prior to blending. The pellets and all of the tablet ingredients, with the exception of magnesium stearate, were then blended in a double cone blender for 30 minutes. The required amount of magnesium stearate was then added in three equal portions with one blender revolution between each addition. Blending was continued for 1 minute after all the magnesium stearate had been added.

The blend was then gravity fed onto a Kilian rotary tablet press. The tablets were produced to the required specifications of weight and hardness. The tablets were passed through a metal checker and a deduster.

Example 2

Compressibility of Various Anti-static Agents

Compression curves were obtained with the use of a Manesty Instrumented tablet press. Tablet blend was fed to the press with stepwise increases in compression force. The compression force was measured via load cells connected to the upper and lower punch holders and their responses logged using proprietary software. Samples of tablets were taken at each compression setting and hardness measured using a Schleuniger hardness tester. A compression curve was then constructed by plotting Compression Force versus the resultant mean hardness (n=10).

The results shown in FIGS. 1 to 4 were obtained as follows.

To determine the effect of different anti-static agents on blend compressibility the agents were each used to "dust" previously un-dusted doxycycline pellets at 0.5% w/w. To ensure that the agent was intimately mixed with the pellets the required quantity of agent was added to pre-weighed pellets and passed back and forth between two metal scoops 40 times. The dusted pellets and other excipients (see Table 2 for the standard tablet blend formulation) were then blended using an Erweka tumble blender with an 8 L cube container. All excipients were screened <850 μm prior to use. Primary blending (minus lubricant) was conducted for 5 minutes at low speed (35 rpm). Secondary blending was conducted for a further 1 minute after the addition of Mg stearate, again at low speed.

TABLE 2

| Ingredient | Content (g) |
| --- | --- |
| Doryx Pellets (Bx A94-031) | 280 |
| Lactose DCL 21 | 585 |
| Starch Purity 21 | 100 |
| Crospovidone (non-micronised) | 30 |
| Mg stearate | 5 |
| Dusting agent (added to pellets separately) | 1.4 |

The resulting tablet blends were compressed using an instrumented Manesty Single Station tablet press fitted with 13 mm round, flat tooling run at 65 min$^{-1}$.

Figure 1:
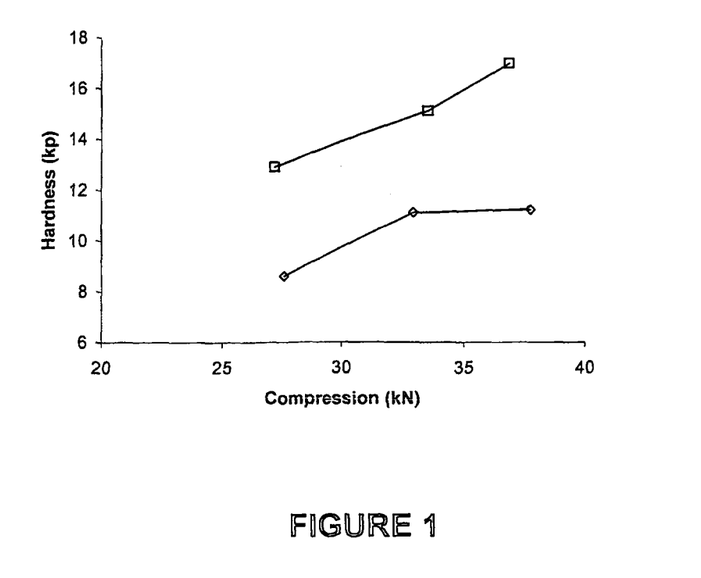
FIG. 1 is a plot of compression vs hardness for tablets formed from pellets that were dusted with talc (◊) and for pellets that were un-dusted (□).
Figure 2:
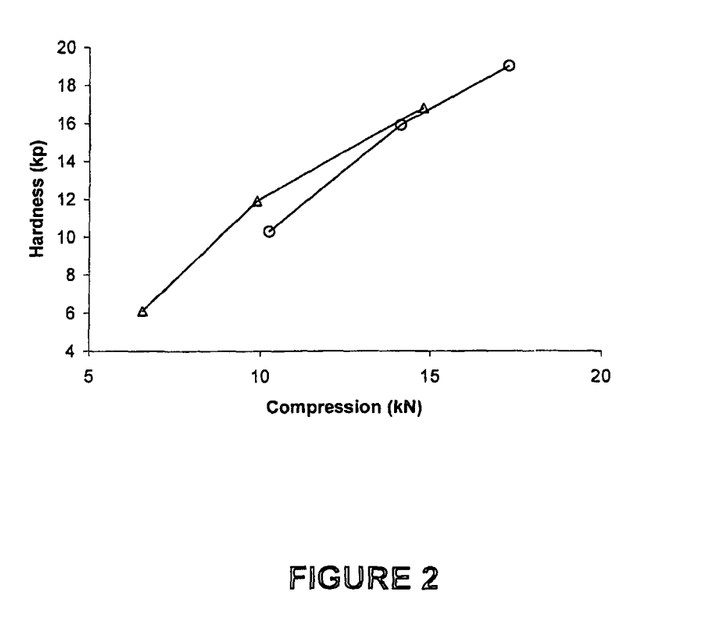
FIG. 2 is a plot of compression vs hardness for tablets formed from pellets that were dusted with microcrystalline cellulose (○) and for pellets that were un-dusted (Δ).
Figure 3:
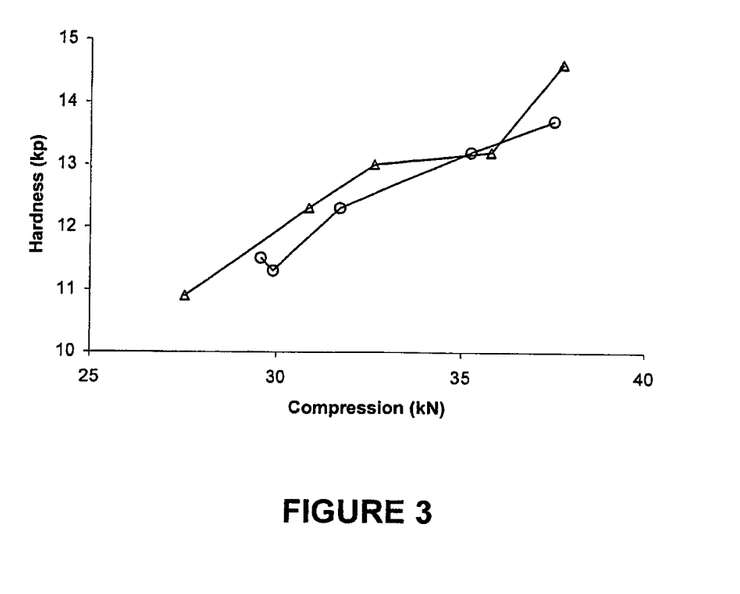
FIG. 3 is a plot of compression vs hardness for tablets formed from pellets that were dusted with starch (○) and for pellets that were un-dusted (Δ).
Figure 4:
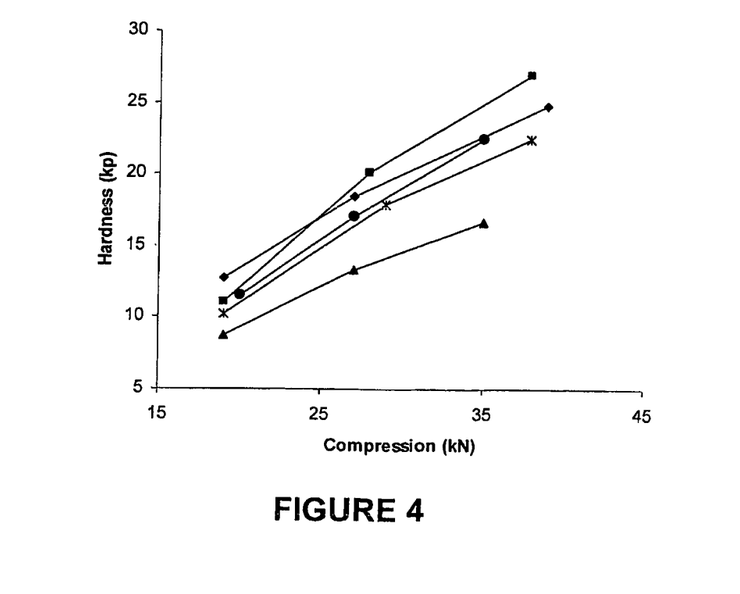
FIG. 4 is a plot of compression vs hardness for tablets formed from pellets that were dusted with talc (Δ), starch (◊), magnesium trisilicate (□), kaolin (*) and for pellets that were un-dusted (○).

As shown in FIG. 1, dusting of pellets with talc to control static decreases the compressibility of the resulting blend. In contrast, FIGS. 2, 3 and 4 show that dusting of pellets with starch, magnesium trisilicate, kaolin or microcrystalline cellulose has little, if any, effect on the compressibility of the resulting tablet blends. Indeed, as best seen in FIG. 4, starch and magnesium trisilicate may actually improve the compressibility of the blend. Thus, the plots demonstrate the negative impact of dusting drug pellets with talc and also the fact that dusting with starch, magnesium trisilicate, kaolin or microcrystalline cellulose is at least equivalent to not dusting at all as far as compressibility is concerned.

Notably, in the case of the blend in this example which contains talc dusted pellets, the hardness of the tablet that is formed does not substantially exceed about 12 kiloponds (kp) despite increasing compression force. In contrast, when the pellets have been dusted with starch or microcrystalline cellulose there is a more linear relationship between the compression force and the resultant hardness of the tablet. Thus, increasing the compression force generally leads to an increase in hardness of the tablet in the case of starch and microcrystalline cellulose dusted pellets, but the same effect is not seen in the case of talc dusted pellets.

Example 3

Anti-static Properties of Various Anti-static Agents

The reduction in static charge that can be achieved with a number of anti-static agents was determined using a Simco SS2X Electrostatic Locator.

Baseline Charge

A number of experiments were conducted and for each experiment approximately 60 g of pellets formed in accordance with Example 1 (Batch # Bx A94-031) were weighed onto a large plastic scoop and then poured to another identical scoop and back again 20 times in rapid succession. This produced the initial static charge which was measured using a Simco SS2X Electrostatic Locator with remote sensor.

Evaluation of Static Reduction

Each anti-static agent was evaluated at 0.5% w/w relative to the pellets. Following measurement of the initial charge as above, 0.3 g of a given anti-static agent was added to the pellets and transferred 5 times between two 200 mL glass beakers to disperse the agent.

Static measurements were conducted only after the charged pellets had been transferred to a glass Petri Dish. Measurements were made using the remote sensor of the Electrostatic Locator with maximum opening to the charge plate and attenuation set to '1×'.

The results of the static charge measurements for the Doryx pellets before and after dusting with various anti-static agents are shown in Table 3.

TABLE 3

| Agent | Initial charge (V) | Final charge (V)* | Reduction (%) |
| --- | --- | --- | --- |
| Talc | 340 | 30 | 91 |
| Starch | 340 | 120 | 65 |
| Microcrystalline cellulose PH101 | 280 | 160 | 43 |
| Kaolin | 340 | 20 | 94 |
| Mg stearate | 300 | 130 | 57 |
| Mg trisilicate | 300 | 40 | 87 |
| Talc (repeat) | 340 | 20 | 94 |

*after dusting with 0.5% w/w anti-static agent

The results showed that talc, kaolin and magnesium trisilicate were all effective in reducing static charge. Of the other agents tested starch was superior to both magnesium stearate and microcrystalline cellulose.

Comparative Example 1

Evaluation of Static Reduction in Dusted Pellets vs Pellets Coated with Anti-static Agent This example contrasts the effect of talc as an anti-static agent when incorporated within the polymer coating of pellets compared to its effect as a powder dusted on the surface of the pellets.

The static charge was measured using a Simco SS2X Electrostatic Locator with remote sensor.

To determine whether the presence of talc in the coating would prevent the pellets from accumulating a static charge 60 g of the pellets of Example 1 were weighed onto a large plastic scoop and then poured to another identical scoop and back again 20 times in rapid succession. This produced the initial static charge in the same way that charging had been conducted in Example 3.

Evaluation of Static Reduction

To disperse the talc through the pellets after charging, 0.3 g of talc was added to the pellets which were then transferred 5 times between two 200 mL glass beakers.

Static measurements were conducted only after the pellets had been transferred to a glass Petri dish. Measurements were made using the remote sensor of the Electrostatic Locator with maximum opening to the charge plate and attenuation set to '1×'.

The results of static charge measurements for doxycycline pellets prepared according to Example 1 and talc-coated doxycycline pellets before and after dusting with talc are shown in Table 4. Doxycycline pellets prepared according to Example 1 differ from talc-coated doxycycline pellets in that there is no talc in the outer polymer coating in the former. In contrast, the outer polymer coating of the talc-coated doxycycline pellets contains 50% w/w (with respect to polymer) of talc. If talc contained in the coating was effective in controlling static the talc-coated doxycycline pellets would charge to a lesser extent and/or be easier to discharge compared to doxycycline pellets prepared according to Example 1.

TABLE 4

| | Initial charge (V) | Final charge (V)* | Reduction (%) |
|---|---|---|---|
| Talc in outer coating | 300 | 60 | 80 |
| No talc in outer coating | 340 | 30 | 91 |

*after dusting with 0.5% w/w talc

Based on these results, it is evident that the presence of talc within the coating had minimal impact on static charge/discharge in contrast to dusting with talc on the outside of the pellets which significantly reduced static regardless of the substrate.

It is not believed that the slightly lower Initial charge on talc-coated doxycycline pellets pellets (300V vs 340V) was significant given the variability of the method. Equally it is not thought that the percent reduction in static charge after dusting with talc was significantly less for the talc-coated doxycycline pellets versus doxycycline pellets prepared according to Example 1 (80% vs 91%). These variations are less significant compared to the extent of reduction in static caused by dusting with the agent.

Finally, it will be appreciated that various modifications and variations of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are apparent to those skilled in the fields of formulation or related fields are intended to be within the scope of the present invention.

The claims defining the invention are as follows:

1. A process for producing a tablet containing an active ingredient, the process comprising:
    providing core elements containing the active ingredient;
    coating the core elements with a pharmaceutically acceptable coating layer;
    drying the coated core elements;
    dusting the dried coated core elements with a powdered anti-static agent selected from the group consisting of kaolin, magnesium trisilicate, starch, microcrystalline cellulose, bentonite, silicon dioxide, cellulose, stearic acid, sodium stearyl fumarate, and glycerol behenate, the group not including talc, to form dusted pellets; and then
    compressing the dusted pellets with tabletting excipients to form the tablet, wherein amount of the anti-static agent is about 0.5% (by weight) of the dusted pellets, and amount of the dusted pellets in each tablet is in the range of 20 to 50% by weight of the total tablet weight.

2. The process according to claim 1, wherein the step of dusting the dried coated core elements with an anti-static agent to reduces accumulated static charge, or prevents or reduces the accumulation of static charge.

3. The process according to claim 1, wherein the drying step is carried out in a fluid bed dryer.

4. The process according to claim 1, wherein the anti-static agent is selected from the group including starch, microcrystalline cellulose, magnesium trisilicate and kaolin.

5. The process according to claim 1, wherein the anti-static agent is starch.

6. The process according to claim 1, wherein the compression force at which the tablet is formed is less than 40 kiloNewtons.

7. The process according to claim 1, wherein the strength of the tablet is about 5 to about 15 kiloponds.

8. The process according to claim 1, wherein the active ingredient is a pharmaceutically active ingredient.

9. The process according to claim 8, wherein the pharmaceutically active ingredient is selected from the group consisting of doxycycline, tetracycline, oxytetracycline, minocycline, chlortetracycline, demeclocycline, and pharmaceutically acceptable salts thereof.

10. The process according to claim 1, wherein the active ingredient is present in the core element in an amount from 5 to 95% by weight, based on the total weight of the core element.

11. The process according to claim 1, wherein the percentage of coated pellets in each tablet is in the range of 25 to 35% by weight of the total tablet weight.

12. The process according to claim 1, wherein the percentage of coated pellets in each tablet is about 30% by weight of the total tablet weight.

13. The process according to claim 1, wherein the tabletting excipients are present in an amount of 50 to 80% by weight of the total tablet weight.

14. A tablet that is formed according to the process of claim 1.

15. The tablet according to claim 14, wherein the anti-static agent is selected from the group including starch, microcrystalline cellulose, magnesium trisilicate and kaolin.

16. The tablet according to claim 14, wherein the anti-static agent is starch.

17. The tablet according to claim 14, wherein the strength of the tablet is about 5 to about 15 kiloponds.

18. The tablet according to claim 14, wherein the active ingredient is a pharmaceutically active ingredient.

19. The tablet according to claim 18, wherein the pharmaceutically active ingredient is selected from the group consisting of doxycycline, tetracycline, oxytetracycline, minocycline, chlortetracycline, demeclocycline, and pharmaceutically acceptable salts thereof.

20. The tablet according to claim 14, wherein the active ingredient is present in the core element in an amount from 5 to 95% by weight, based on the total weight of the core element.

21. The tablet according to claim 14, wherein the percentage of coated pellets in each tablet is in the range of 25 to 35% by weight of the total tablet weight.

22. The tablet according to claim 14, wherein the percentage of coated pellets in each tablet is about 30% by weight of the total tablet weight.

23. The tablet according to claim 14, wherein the tabletting excipients are present in an amount of 50 to 80% by weight of the total tablet weight.

* * * * *

UNITED STATES PATENT AND TRADEMARK OFFICE
CERTIFICATE OF CORRECTION

Page 1 of 1

PATENT NO. : 8,715,724 B2
APPLICATION NO. : 11/666354
DATED : May 6, 2014
INVENTOR(S) : Lukas

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 986 days.

Signed and Sealed this
Eighth Day of September, 2015

Michelle K. Lee
*Director of the United States Patent and Trademark Office*